United States Patent [19]
Jones

[11] Patent Number: 5,201,908
[45] Date of Patent: Apr. 13, 1993

[54] SHEATH FOR PROTECTING ENDOSCOPE FROM CONTAMINATION

[75] Inventor: Jeffrey S. Jones, Salem, Va.

[73] Assignee: EndoMedical Technologies, Inc., Roakoke, Va.

[21] Appl. No.: 713,178

[22] Filed: Jun. 10, 1991

[51] Int. Cl.⁵ .............................................. A61B 1/00
[52] U.S. Cl. ...................................... 128/4; 128/4 A
[58] Field of Search ................ 128/4, 917, 918, 919, 128/844, 4 A

[56] References Cited

U.S. PATENT DOCUMENTS

| | | |
|---|---|---|
| 4,646,722 | 3/1987 | Silverstein et al. ................ 128/4 |
| 4,721,097 | 1/1988 | D'Amelio . |
| 4,741,326 | 5/1988 | Sidall et al. . |
| 4,779,611 | 10/1988 | Grooters et al. .................. 128/4 |
| 4,809,678 | 3/1989 | Klein . |
| 4,825,850 | 5/1989 | Opie et al. . |
| 4,852,551 | 8/1989 | Opie et al. . |
| 4,869,238 | 9/1989 | Opie et al. . |
| 4,886,049 | 12/1989 | Darras .............................. 128/4 |
| 4,991,565 | 2/1991 | Takahashi et al. ................ 128/4 |

FOREIGN PATENT DOCUMENTS

3508833 9/1986 Fed. Rep. of Germany ......... 128/4

Primary Examiner—Richard J. Apley
Assistant Examiner—Karen A. Jalbert
Attorney, Agent, or Firm—Ross & Stevens

[57] ABSTRACT

A protective covering for a medical instrument, such as an endoscope, is described. The covering includes an elongated hollow sheath having a wall of flexible material. The sheath is substantially gas and water impervious and includes a channel for the medical instrument. The sheath further includes auxiliary access channels associated with the sheath for providing a variety of functions, such as instrument manipulation, and fluid removal. The distal end of the protective covering is provided with a cap having an optically clear window to the allow the lens portion of the medical instrument to operate.

5 Claims, 8 Drawing Sheets

SHEATH FOR PROTECTING ENDOSCOPE FROM CONTAMINATION

FIELD OF THE INVENTION

The present invention is directed to medical instruments and more particularly to endoscopes. The present invention is specifically directed to a sanitary disposable covering or sheath for an endoscope, which sheath shields the endoscope from the patient's body and from germs and other disease-bearing organisms. The present invention is also directed to a device for enhancing the functions of an endoscope, such functions including the provision of services including suction, biopsy, air and water.

DESCRIPTION OF THE PRIOR ART

It is an axiom of medicine that medical instruments invading or associating with a patient's body be extremely clean, if not sterilized. This is particularly true with instruments, such as endoscopes, which pass through a body orifice, such as the urethra, anus, etc. Unless these instruments are sterilized between use, the opportunities for passing disease-bearing organisms between patients is enhanced.

Sterilizing medical instruments generally requires gas-sterilization. The process usually takes twenty-four hours and, as such, is not practical for instruments used several times a day. As a result, many instruments are soaked in a germicidal solution that is of questionable efficacy. The soaking takes at least ten minutes, which is advantageous over the gas sterilization process. However, the germicidal solutions tend to be caustic and will cause the premature destruction of the medical instruments.

Several alternatives are contemplated to resolve this problem. The use of disposable instruments, such as disposable endoscopes, has been suggested. However, this would result in an absurd cost, which is not justified. An alternative solution is the application of a sanitary disposable sheath for the medical instruments. As an example, reference is made to U.S. Pat. No. 4,721,097 to D'Amelio, which discloses a disposable endoscope sheath. The sheath is provided with channels extending the length of the sheath, which have the purpose of injecting air or gas into a patient's organs to provide better visibility or to allow the insertion of various mechanisms or devices in the body to perform manipulations.

U.S. Pat. No. 4,741,326 to Sidall et al. is directed to a protective disposable sheath for use with a medical instrument, such as an endoscope. The sheath includes a transparent distal end plate. The end plate can be made of acrylic, glass or plastic material. The sheath also includes a tube extending along the sheath. The tube is adapted to accommodate a biopsy valve or other instrument. Additionally, the end plate has a nozzle means for directing air, water or other cleaning media onto the outer surface of the lens. However, this device allows the interior of the endoscope to become contaminated, which fundamentally differs from the present invention.

U.S. Pat. No. 4,809,678 patent to Klein is directed to a disposable sheath for an endoscope. The proximal end of the sheath is elasticized to prevent seepage of liquids or other contaminants to the instrument. The distal end is transparent in order to allow the endoscope to function properly. Other references which disclose disposable sheaths for an endoscope include U.S. Pat. Nos. 4,869,238 and 4,852,551 to Opie et al.

SUMMARY OF THE INVENTION

It is an object of the invention to develop a disposable covering for an endoscope that will prevent body fluids from contacting the scope while it is in use while preserving the visual capabilities of the scope and enhancing the scope's function.

It is also an object of the present invention to protect the patient from a contaminated scope.

It is further an object of the present invention to lessen the down time for cleaning and sterilization by providing a disposable sanitary protective covering for a medical instrument.

These objects and others are addressed by the present invention which is a protective covering for a medical instrument. The covering includes an elongated hollow sheath having a wall of flexible material. The material is substantially gas and water impervious. The sheath has a proximal end and a distal end, wherein the distal end comprises an end-fitting cap having a first end, second end and sidewalls. The first end of the end-fitting cap includes an optically clear element. The second end of the cap is in sealing engagement with the distal end of the sheath. The protective covering also includes at least one axially-directed access channel associated with the sheath and extending along side the sheath. The access channel has a distal and a proximal end, wherein the distal end of the access channel may extend beyond the distal end of the sheath.

The protective covering prevents any contaminant material from touching any part of the interior or exterior of the endoscope. It is easily placed over the endoscope and provides enhanced biopsy, suction and lens-cleaning capabilities over just the scope itself. The covering provides externally-mounted air-water-suction-biopsy channels that fit over the endoscope but by-pass the internal channels provided by various scopes in the prior art. In this manner, the external channels do not get in the way of the viewing function of the endoscope.

The end cap also allows for a watertight seal. Further, the present invention allows the lens of the endoscope to be placed adjacent the end plate of the end cap. In this manner, the lens of the endoscope retains its visual acuity, even when placed in the protective covering of the present invention.

Further objects, features and advantages of the invention will be apparent from the following detailed description when taken in conjunction with the accompanying drawings.

BRIEF DESCRIPTION OF THE DRAWINGS

In the drawings.

FIG. i is a plan view of a disposable covering for shielding an endoscope.

DETAILED DESCRIPTION OF THE INVENTION

The present invention provides a disposable protective covering or sheath for shielding an endoscope from the patient's body and the body from the endoscope. The covering includes a transparent end so that the optics of the endoscope will not be impaired. Further, the covering includes at least one access channel for fluids or instruments to be introduced to the body. The covering may be attached to the endoscope in a simple sealing engagement. As an example, an elastic band will provide the sealing engagement.

The present invention applies to a variety of endoscopes for examining the body. Such examples include cytoscopes, upper endoscopes for the examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces.

Figure 1:
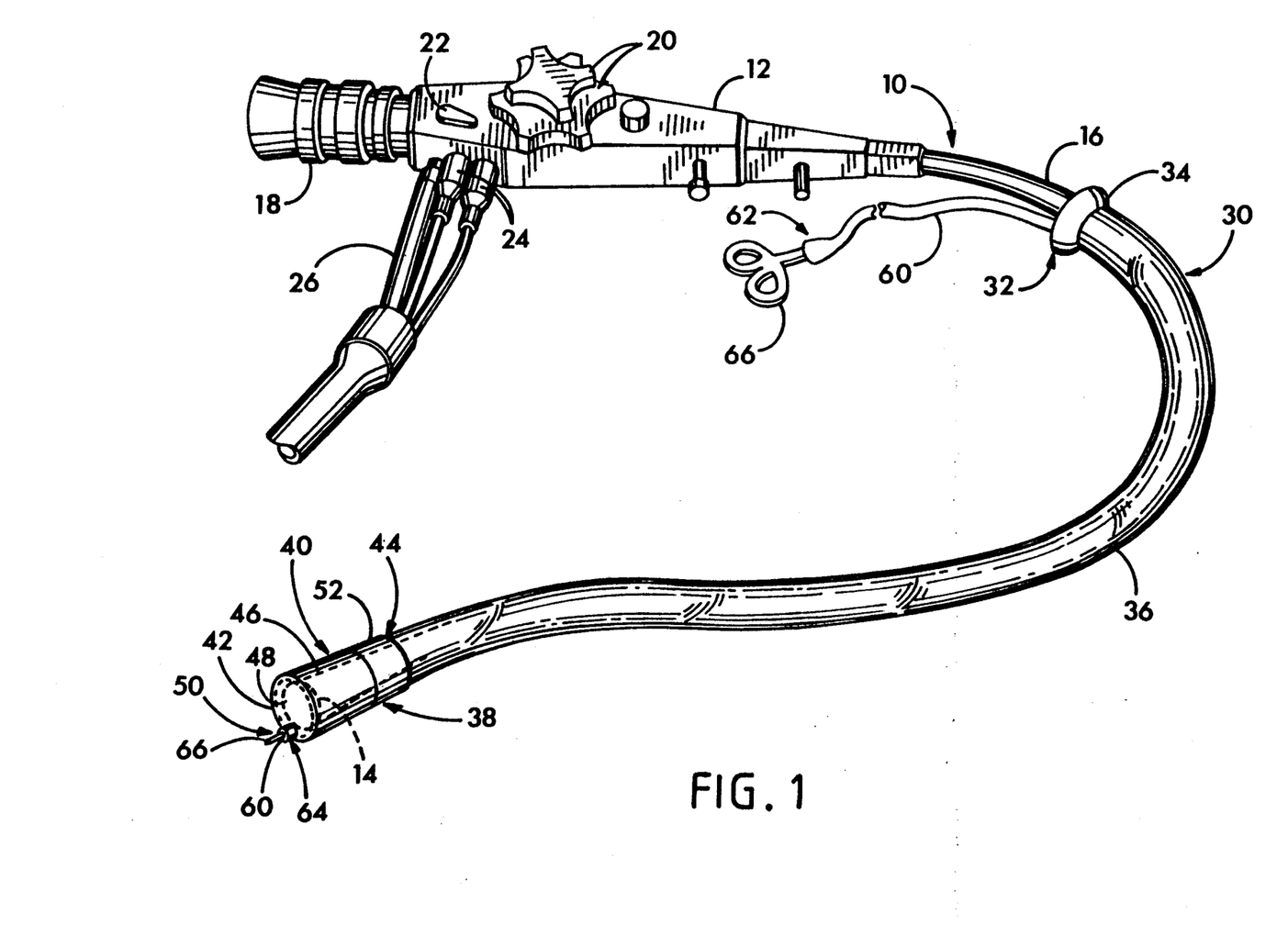

Referring now to the drawings, FIG. 1 illustrates an endoscope, which includes a conventional, flexible, basic endoscope, generally designated 10, and commonly used in the medical field. The endoscope includes an operating end 12 which permits, by manipulation of the physician, a variety of operations to be performed. The endoscope also includes a distal end 14, illustrated in phantom. The operating end 12 and the distal end 14 are joined by an elongated flexible portion 16. Generally, the operating end 12 includes an eye piece assembly 18, one or more control knobs 20, an inlet opening 22 through which an instrument such as a forceps is inserted, and air and/or water feed control devices 24, a suction control (not illustrated) and a light inlet means 26. The construction of the endoscope 10 is well-known to the art and does not form a part of this invention. Reference is made to U.S. Pat. No. 4,809,678 to Klein, U.S. Pat. No. 4,825,850 to Opie, et al., and U.S. Pat. No. 4,852,551 also to Opie, et al. for a variety of descriptions of endoscopes.

According to the present invention, a flexible, protective covering 30 is provided to protect the endoscope 10 from contamination. The entire flexible portion of the endoscope 10 will be covered. The covering 30 includes a proximal end 32 which can be sealingly engaged to the flexible portion 16 of the endoscope 10 by means of a constriction band 34 or the like.

The protective covering 30 includes an elongated hollow sheath portion 36 having a wall of generally flexible and resilient material. Included within the wall of the sheath is an endoscope channel 37, illustrated in FIGS. 7 and 8, for receiving the elongated, flexible portion 16 of the endoscope 10.

Preferably, the material comprising the sheath 36 is an elastomeric material, which is substantially gas and water impervious to prevent the invasion of contaminants to and from the endoscope 10. Suitable elastomeric materials include polymeric resinous materials such as natural and synthetic rubbers, thermal plastic polymeric materials such as polyethylene, polypropylene, polyurethane and combinations of natural or synthetic rubbers with thermal plastic polymeric materials such as rubber-modified polyethylene, rubber-modified polystyrene and the like.

Located on the opposite end of the proximal end 32 of the sheath 36 is the distal end 38. The distal end 38 includes a cap 40 having a first end 42, a second end 44, and a generally cylindrical wall 46. The first end 42 includes a window 48 of optically clear glass or plastic to serve as a window for the endoscope optics located at the distal end 14 of the endoscope. In this manner, the protective covering will serve as a protection against contamination while still allowing the endoscope end to perform the required task of viewing. The window 48 may be made of a number of materials known to the art. Preferred examples of materials include styrene, plexiglass and polyvinyl chloride. It is also within the scope of the present invention to provide a window 48 with magnifying capabilities.

It is within the scope of the present invention to provide the window 48 at the first end 42 or along the side wall 46 as required by the purpose of the endoscope. As such, some endoscopes are constructed such that the optical element is a side-viewing optical element.

The cap portion is provided with a utility opening 50 which extends from the first end 42 of the cap. This opening 50 will be described in more detail hereinafter.

Figure 2:
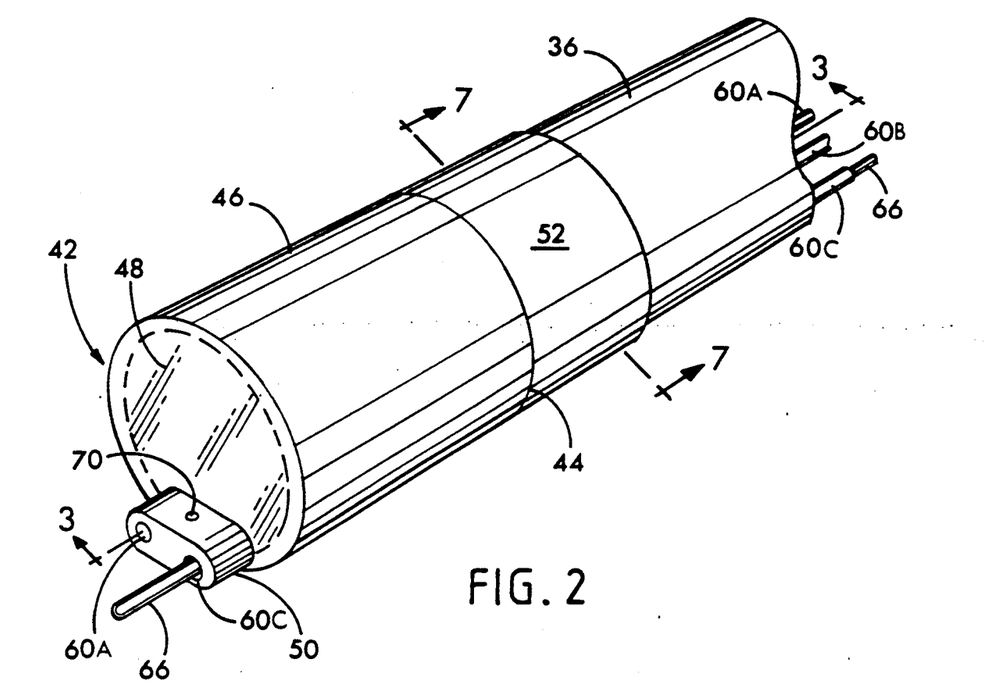
FIG. 2 is an enlarged perspective view of the distal portion of one embodiment of the endoscope covering.
Figure 3:
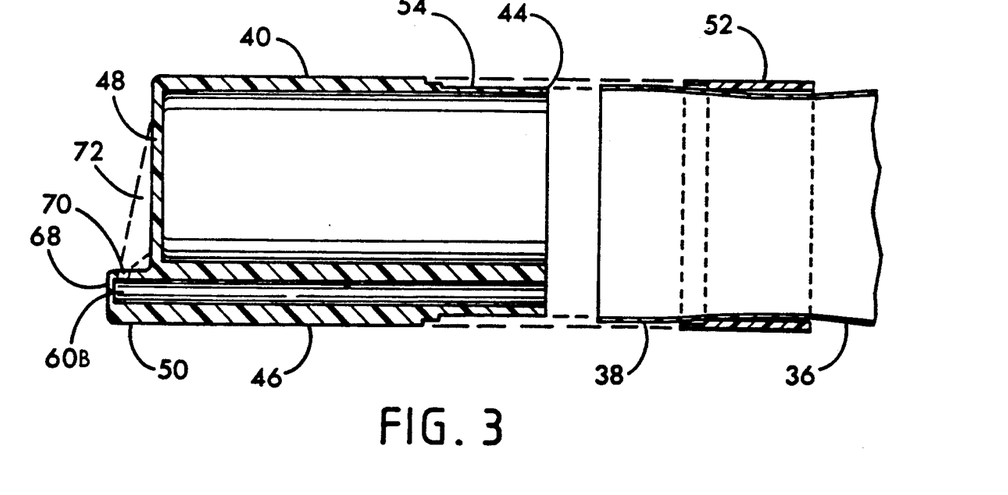
FIG. 3 is a partially exploded cross-sectional view of the distal portion of the endoscope covering of FIG. 2 taken along lines 3—3 of FIG. 2 and illustrating one embodiment of an attachment collar.

The second end 44 of the cap 40 is preferably sealingly engaged with the distal portion 38 of the sheath 36 by a snap-fit collar 52 as illustrated in FIGS. 2 and 3. As illustrated in FIG. 3, the second end 44 of the cap 40 includes a collar reception area 54 of reduced diameter to accept the distal end 38 of the sheath 36. The collar then slides over the area 54 with the distal end 38 of the sheath therebetween to adhere the sheath 36 to the cap 40 in sealing engagement.

Alternatively, the cap 40 may be sealingly engaged with the distal portion 38 by means known to the art, such as glue or other sealants.

The cap 40 is preferably constructed of a flexible semi-rigid plastic or rubber material, to form some structural integrity over the end of the endoscope 10. Materials such as described with respect to the sheath 36 may be used to form the cap 40.

As mentioned previously, the sheath 36 is preferably attached to the cap 40 by means of a collar 52. The placement is facilitated by providing the collar reception area 54 of a diameter slightly smaller than the diameter of the wall 46. The collar reception area 54 provides a "male" mating portion to the "female" collar 52, which is intended to slide over the reception area 54. Prior to fitting the collar 52 on the reception area 54, the distal end 38 of the sheath 36 is placed in surrounding engagement over the collar reception area 54. At this point, the collar 52 is placed on the cap in order to sealingly engage the sheath 36 to the cap 40.

Figure 4:
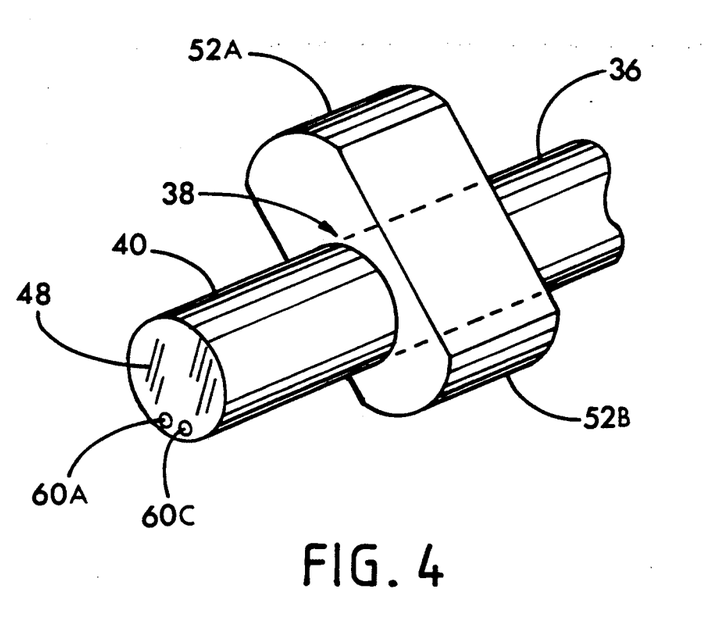
FIG. 4 is a partially exploded perspective view of the distal portion of another embodiment of the endoscope cap illustrating another collar embodiment.

The collar 52 may also be separated into an upper collar portion 52A and a lower collar portion 52B, as illustrated in FIG. 4, which halves join in a snap-fit engagement according to means well known to the art to seal the sheath 36 to the cap 40.

Figure 6:
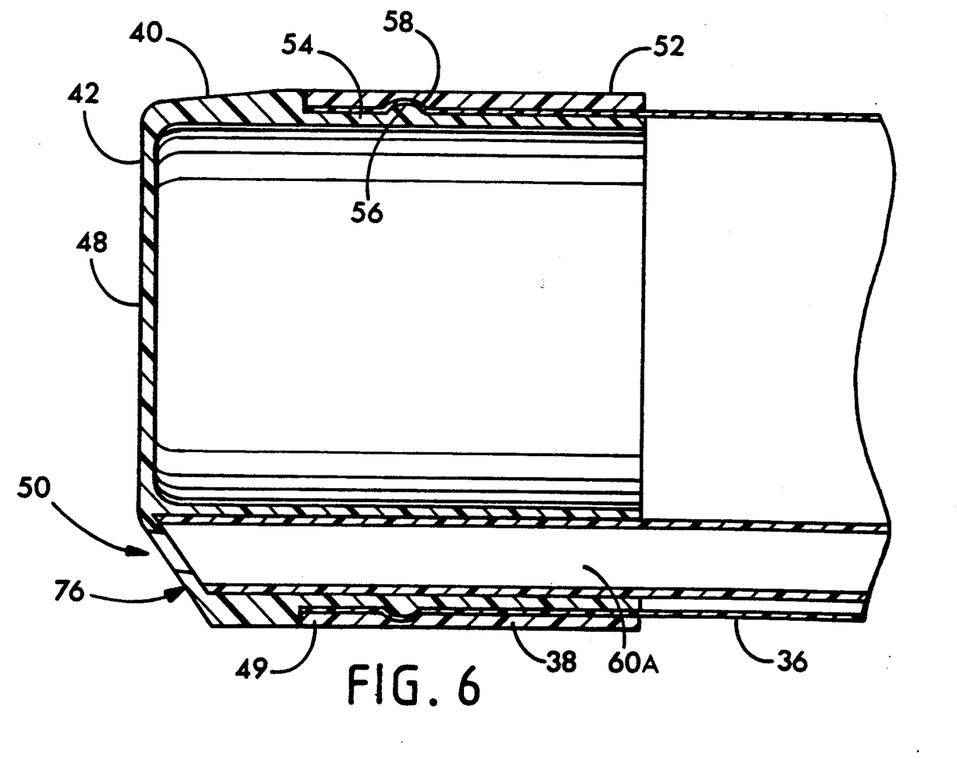
FIG. 6 is a cross-sectional view of the alternative embodiment of the distal portion of the endoscope covering of FIG. 5 taken along lines 6—6.

Referring now to FIG. 6, there is illustrated another embodiment of the collar reception area 54. The collar reception area 54 of the cap 40 may be provided with a circumferential ridge 56. The collar 60 is likewise provided with an analogous depression area 58. The sheath 36 is then placed on the cap 40 in the manner described previously. The collar is then snap fit over the ridge 56 to provide sealing engagement.

The protective covering 30 of the present invention also includes at least one and preferably more axially directed access channels 60 extending in axial fashion along the sheath 36 and ending at the opening 50. As illustrated in FIG. 1, the covering 30 of the present invention may include one access channel 60. The covering 30 may, however, have more than one access channel 60 associated with the protective covering 30, as illustrated in FIG. 2.

Figure 7:
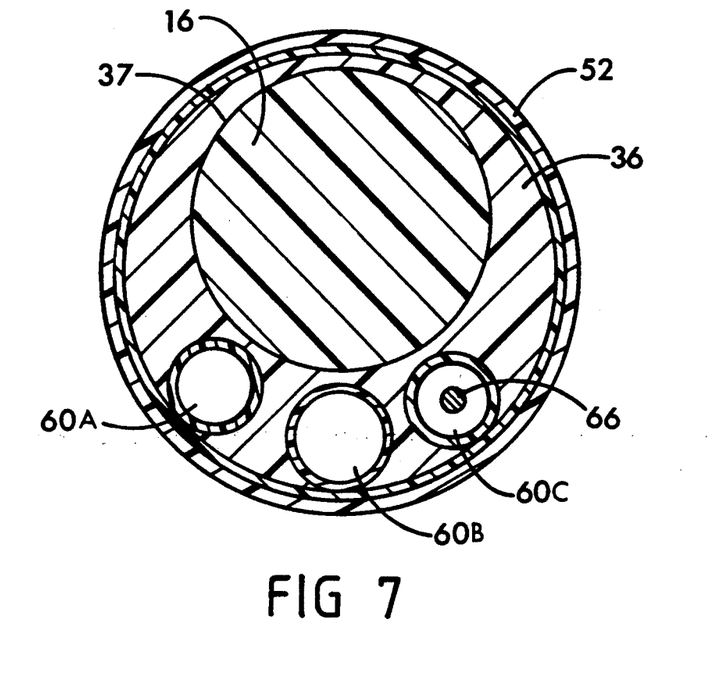
FIG. 7 is a cross-sectional view of the endoscope covering taken along lines 7—7 of FIG. 2.
Figure 8:
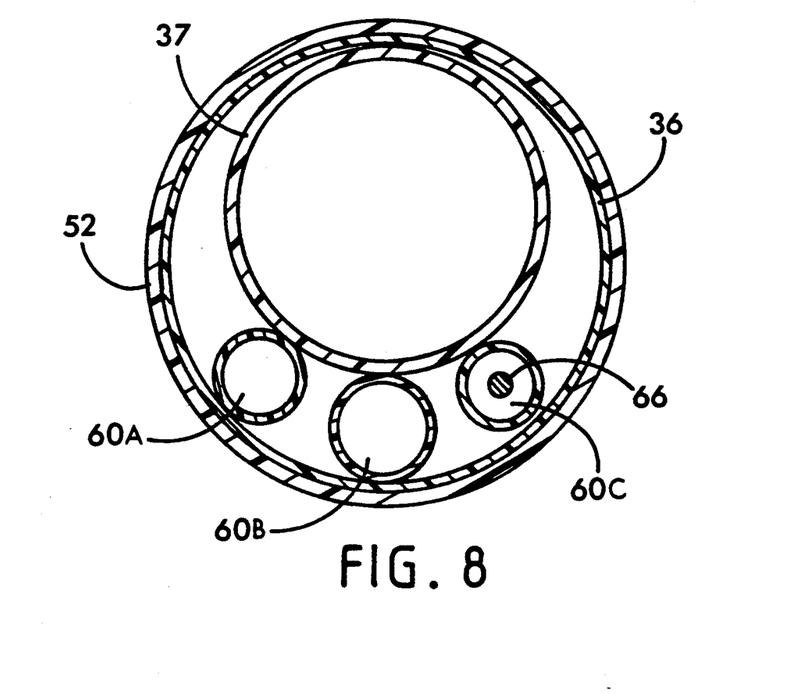
FIG. 8 is a cross-sectional view of another embodiment of the endoscope covering taken along lines 7—7 of FIG. 2.

The access channels 60 have a proximal end 62, associated with the proximal end 32 of the covering 30 and a distal end 64, associated with the distal end 38 of the protective covering 30. As illustrated in FIG. 7, the access channels 60 may be formed directly within the sheath 36 and end cap 40. Alternatively, the access channels 60 may be separate tubular channels extending axially between the main endoscope channel 37 and the wall of the sheath 30 as illustrated in FIG. 8.

The proximal end 62 of the access channel 60 may be attached or otherwise associated with the endoscope 10 for ease of use by the surgeon. Otherwise, it can be loose, i.e., not attached to the endoscope as illustrated in FIG. 1. One purpose of the access channel 60 is to allow passage of a biopsy tool or instrument 66 through the channel to the distal end 64. In this manner the tool can be manipulated by a surgeon to perform a surgical task such as a biopsy.

FIGS. 2-3 illustrate a preferred embodiment of the cap 40 of the present invention, including at least three access channels 60A, 60B, 60C and the endoscope channel 37 to receive the flexible portion 16. Each access channel 60 achieves a required purpose. It is an important feature of the present invention that the access channels 60 extend alongside the endoscope's flexible portion 16 rather than through the endoscope as in many prior art instruments. In this manner, the access channels 60 do not get in the way of the optical elements of the endoscope 10.

As illustrated in FIG. 2, there are three access channels 60A, 60B, 60C, each of which provide a required service. In this embodiment, access channel 60A is attached to a suction or pump element (not shown) in the endoscope body portion for providing and withdrawing fluids to and from the patient's body.

Access channel 60B provides a means for cleaning the optically clear window 48. As illustrated in FIG. 3, access channel 60B includes an end cap 68 to prevent the exit of fluids from the front portion of the opening 50. Rather, access channel 60B is provided with a spray port 70 for issuing a spray of cleaning fluid, illustrated in phantom at 72, to the window 48. The cleaning fluid is pressurized by means of a pump system (not illustrated) in association with the endoscope 10.

Access channel 60C is provided for manipulating instruments, illustrated in FIGS. 1, 2 and 7-8 at 66. The instruments are manipulated by the surgeon via access means at the proximal end 62 of access channel 60C. The instrument may be in the form of a forceps, which is inserted into the body for medical treatment. The forceps is manipulated by the surgeon, who can see the end of the forceps via the window 48.

As illustrated in FIGS. 2 and 3, the utility opening 50 is designed to extend beyond the first end 42 of the cap 40 a short distance. This extension provides a number of advantages. First, the extension provides a location for providing the spray port 70 to provide spraying access to the exterior of the window 48. Second, the extension opening 50 provides a manipulating feature for the instrument 66. In this manner, the surgeon, viewing the extension opening 50, can determine exactly when the instrument 66 exits the end of the access channel 60C. This may provide advantages in enhancing the manipulation of the instrument.

Figure 5:
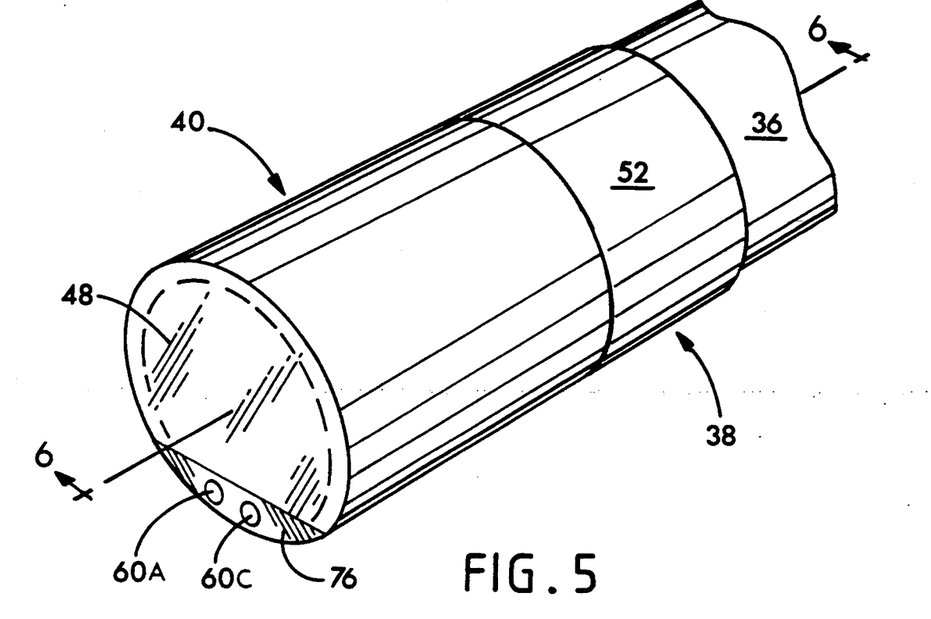
FIG. 5 is an enlarged perspective cross-sectional view of a second alternative embodiment of the distal portion of the endoscope covering illustrating an alternative means for attaching the cap portion on the distal end of the covering to the covering.

Referring now to FIGS. 5 and 6, there is illustrated an alternative embodiment of the distal end 38 of the protective covering 30. Rather than having an extended utility opening 50 as illustrated in FIG. 2, the opening 50 at the first end 42 is characterized by an angled planar zone 76. In this embodiment, the access channels 60 end at a position behind rather than in front of the window 48.

It is also within the scope of the present invention to place the utility opening on the same plane as the window 48, as illustrated in FIG. 4. Thus, the utility opening 50 can be flush with the surface of the window 48.

A method of using the covering 30 will now be described. In the embodiment illustrated in FIG. 1, the cover 30 is applied to the flexible portion 16 of the endoscope 10 by slipping the endoscope channel 37 of the sheath 36 over the flexible portion 16. It is also anticipated that the cover may be provided in a rolled-up manner to be applied to the flexible portion 16 by unrolling the sheath. After the cover 30 has been placed on the flexible portion 16 of endoscope 10, the endoscope is then used in a normal medical procedure known to those skilled in the art.

After the medical procedure has been completed, the sheath can be removed by peeling it away from the endoscope flexible portion 16. The entire covering 30 can then be disposed. It is also within the scope of the present invention to provide reusable coverings 30 which can be re-sterilized for subsequent use.

Figure 9:
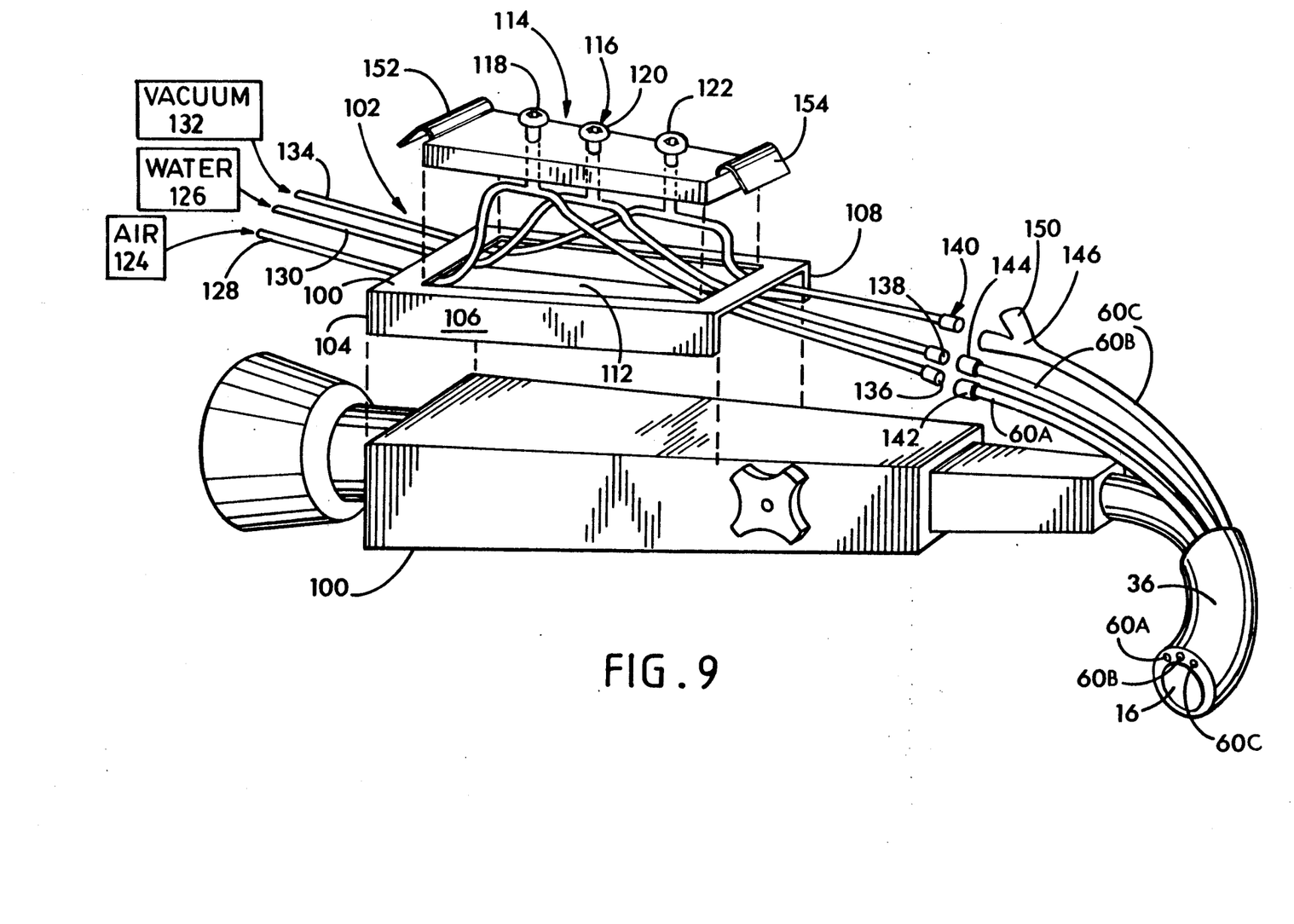
FIG. 9 is a partially exploded perspective view of another embodiment of the protective device for an endoscope of the present invention.
Figure 10:
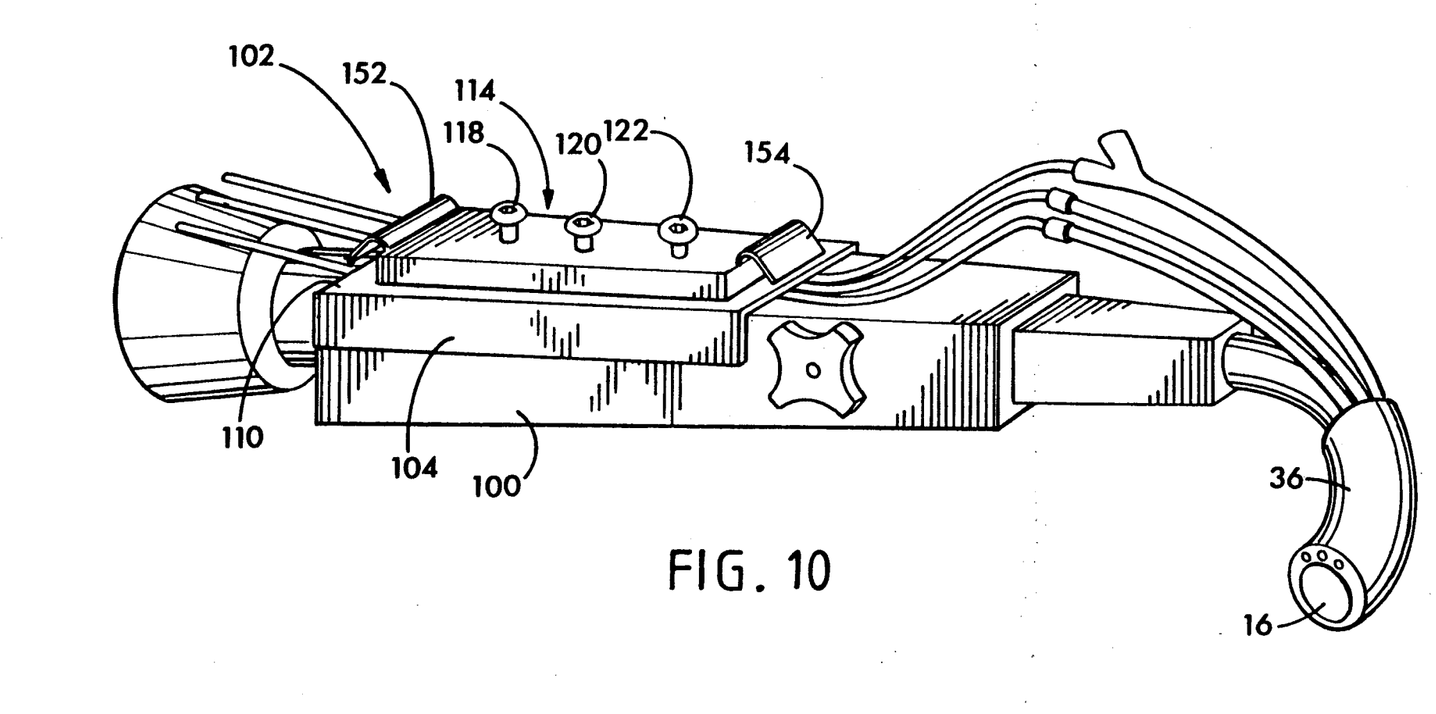
FIG. 10 is an intact perspective view of the embodiment of FIG. 9.

Reference is now made to FIGS. 9 and 10 for an alternative embodiment of the protective covering for the endoscope. FIGS. 9 and 10 illustrate a standard endoscope 100, known to the art and described herein. Unlike the endoscope 10 described and illustrated in FIG. 1, the endoscope 100 does not require air and water feed control devices integrated with the scope. These features are provided by a removable attachment, generally designated at 102. The attachment 102 includes a manifold cover 104 designed to be secured, frictionally or otherwise, to the outer surface of the endoscope body. The manifold cover 104 includes securing side pieces 106, 108 and an upper surface 110 with an opening 112. The opening 112 is designed to receive a manifold 114 which includes a valve system 116.

The valve system 116 is a series of valves, which are manipulated by a surgeon to perform a series of tasks. As illustrated in FIGS. 9 and 10, there are three valves 118, 120, 122. It is within the scope of the invention to provide more or fewer valves depending on the endoscope used and the requirements of the operation. The action and operation of the valve system 116 are well known to the art and, with the exception of the manner of placement on the endoscope 100, do not form part of this invention. Reference is made to U.S. Pat. Nos. 4,825,850, 4,852,551 and 4,869,238 to Opie et al., which are incorporated herein for a description of valve systems in endoscopes.

As herein illustrated, valves 118 and 120 are designed to provide air and water, respectively, to the patient from an air source 124 and a water source 126 through air communicating channel 128 and water communicating channel 130. Valve 122 is a suction valve attached to a vacuum system 132 by means of suction channel 134.

Each of the communicating channels 128, 130, 134 are provided with connectors 136, 138, 140 to detachably connect the channels to the access channels 60. The access channels 60 are provided with receptors 142, 144, 146 to receive the connectors 136, 138, 140 in a snug, sealed fit. In this manner the sheath 36 with attached access channels 60 is detachably connected to the attachment 102. After use, the sheath 36 can be disposed, and the attachment 102 can be reused.

It is within the scope of the present invention to provide one of the receptors, here: 146, with a biopsy instrument access port 150. Therefore, access channel 60C serves the dual purpose of providing a vacuum if required or providing a channel for a biopsy instrument.

The manifold 114 may be provided with winged tabs 152, 154 to assist the surgeon in manipulating the valves 118, 120, 122 in use. In operation, the surgeon may place the little finger and thumb of one hand under the tabs 152, 154 to assist in manipulating the endoscope 100. The remaining fingers will then be available to manipulate the valves 118, 120, 122 in much the same manner that one would play a horned instrument such as a trumpet.

Figure 11:
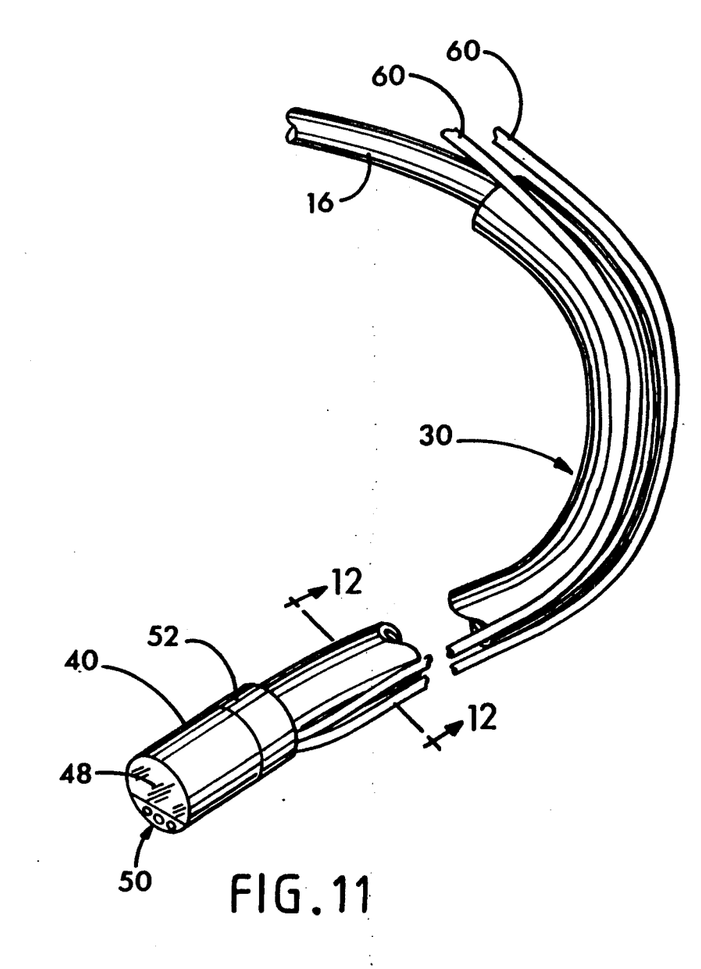
FIG. 11 is a perspective view of another embodiment of the protective sheath of the endoscope covering of the present invention.
Figure 12:
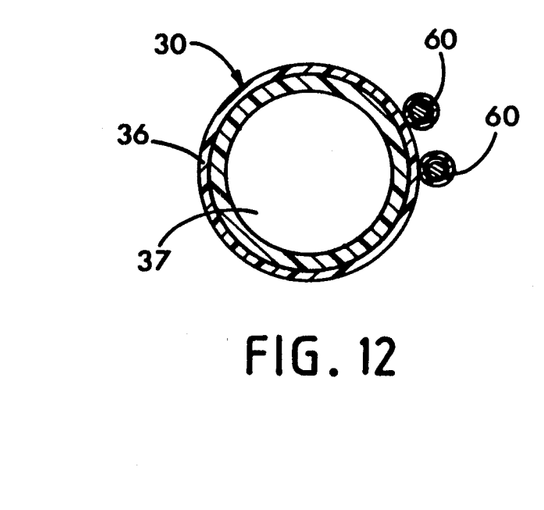
FIG. 12 is a cross-sectional view of the embodiment of FIG. 11 taken along line 12—12.

Reference is now made to FIGS. 11 and 12 for yet another embodiment of the protective cover 30 of the present invention. This embodiment differs from the embodiments featured in FIGS. 7 and 8 in that the access channels 60 are exterior to the outer wall of the sheath 36. The channels 60 may, but do not necessarily have to be, attached to the outer wall of the sheath 36. It is envisioned in this invention that the access channels 60 would enter the cap 40 at the location of the collar 52 and terminate at the utility opening 50.

It is understood that the invention is not confined to the particular construction and arrangement herein illustrated and described, but embraces such modified forms thereof as come within the scope of the following claims.

What is claimed is:

1. A detachable valve system for a conventional endoscope, wherein the endoscope includes an endoscope body and an elongated portion having a distal end and a proximal end, the proximal end being attached to the endoscope body, wherein the valve system is adapted for use with a protective covering for the endoscope, wherein the protective covering includes a sheath adapted to encompass the elongated portion of the endoscope, the sheath including a proximal end and a distal optical end, wherein the distal optical end is adapted to be placed adjacent the distal end of the elongated portion of the endoscope such that the endoscope retains its visual acuity when the covering is in place on the endoscope, the protective covering further including at least one axially-directed instrument manipulation access channel adapted to extend alongside and exterior to the elongated portion of the endoscope, the valve system comprising:

(a) a manifold cover adapted to detachably connect at least one valve to the endoscope body, wherein the valve communicates with the access channel of the protective covering to enable the endoscope user to perform a required task;

(b) connecting means to detachably connect the valve to the at least one access channel; and (c) means to secure the manifold cover to the endoscope body.

2. The valve system of claim 1, wherein the valve comprises means to provide an air source, water source or suction source to the access channel.

3. The valve system of claim 1, wherein the manifold cover comprises a plurality of valves.

4. A combination valve system and protective covering for a conventional endoscope having an endoscope body and an elongated portion having a distal end and a proximal end, wherein the proximal end is attached to the endoscope body, the combination comprising:

(a) an elongated hollow sheath having a wall of flexible material, the material being substantially gas and water impervious, the sheath including a main channel for the elongated portion of the endoscope, a proximal end and a distal end, wherein the distal end of the sheath comprises an end-fitting cap having a first end, second end, and side walls, the first end including an optically clear element adapted to be placed adjacent the distal end of the endoscope such that the endoscope retains its visual acuity when the covering is in place on the endoscope, and wherein the second end of the cap is in sealing engagement with the distal end of the sheath, and at least one axially-directed instrument manipulation access channel associated with the sheath and cap and adapted to extend alongside and exterior to the elongated portion of the endoscope, the access channel having a distal and a proximal end, wherein the distal end of the access channel is peripherally located on the first end of the cap and extends beyond the first end of the cap a sufficient distance to enable the user to observe the instrument initially extending from the distal end of the access channel; and (b) a detachable valve system comprising a manifold cover adapted to detachably connect at least one valve to the endoscope body, wherein the valve communicates with the access channel of the protective covering to permit the endoscope user to perform a required task, connecting means to detachably connect the valve to the access channel, and means to secure the manifold cover to the endoscope body.

5. The protective covering of claim 4 wherein the sheath is disposable.

* * * * *